(12) United States Patent
Nishino et al.

(10) Patent No.: US 8,373,138 B2
(45) Date of Patent: Feb. 12, 2013

(54) VESSEL STERILIZATION APPARATUS

(75) Inventors: Yukinobu Nishino, Kanazawa (JP); Tokuo Nishi, Kanazawa (JP); Yukihiro Yamamoto, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 314 days.

(21) Appl. No.: 12/448,308

(22) PCT Filed: Dec. 27, 2007

(86) PCT No.: PCT/JP2007/075125
§ 371 (c)(1),
(2), (4) Date: Oct. 30, 2009

(87) PCT Pub. No.: WO2008/081868
PCT Pub. Date: Jul. 10, 2008

(65) Prior Publication Data
US 2010/0072395 A1 Mar. 25, 2010

(30) Foreign Application Priority Data
Dec. 28, 2006 (JP) .................. 2006-354653

(51) Int. Cl.
*H01J 37/20* (2006.01)
(52) U.S. Cl. ......... 250/455.11; 250/454.11; 250/453.11; 250/492.1; 250/492.3
(58) Field of Classification Search ............. 250/453.11, 250/454.11, 455.11, 492.1, 492.3
See application file for complete search history.

(56) References Cited

U.S. PATENT DOCUMENTS 7,145,155 B2 * 12/2006 Nablo et al. ............... 250/492.1
2006/0159583 A1 7/2006 Naslund et al.

FOREIGN PATENT DOCUMENTS

| JP | 52-017469 | 5/1977 |
|----|-----------|--------|
| JP | 61-226050 | 10/1986 |
| JP | 09-222500 | 8/1997 |
| JP | 2003-054521 | 2/2003 |
| JP | 2005-329140 | 12/2005 |
| JP | 2005-335724 | 12/2005 |
| JP | 2006-199377 | 8/2006 |
| JP | 2006-518689 | 8/2006 |

\* cited by examiner

*Primary Examiner* — Robert Kim
*Assistant Examiner* — Hanway Chang
(74) *Attorney, Agent, or Firm* — Flynn, Thiel, Boutell & Tanis, P.C.

(57) ABSTRACT

An irradiation surface of an electron beam irradiation device 28 is directed toward a vessel 2 conveyed by a vessel conveying device 24 to thereby irradiate the vessel 2 with the electron beam to sterilize the vessel, an irradiation chamber 30 is provided so as to surround the irradiation surface of the electron beam irradiation device 28 and the vessel 2 subjected to the irradiation, a discharge chamber 32 is provided on an outlet side of the irradiation chamber 30, and dry-air supply means 80 for supplying a dried aseptic air is connected to the irradiation chamber 30. By removing moisture within the irradiation chamber 30 which is irradiated with the electron beam, the changing of nitrogen oxide to nitric acid is suppressed to thereby prevent metal portions from corroding.

4 Claims, 4 Drawing Sheets

VESSEL STERILIZATION APPARATUS

TECHNICAL FIELD

The present invention relates to a vessel sterilization apparatus for performing sterilization of vessels by irradiating them with electron beam during the conveyance thereof.

BACKGROUND TECHNOLOGY

In a sterilization apparatus using an electron beam, when the electron beam is irradiated onto a work piece to be sterilized, nitrogen oxide is generated. The nitrogen oxide is then dissolved, in an atmosphere having a water content, into water, and changes into nitric acid. Since the nitric acid has a corrosive nature, the life time of a sterilization apparatus becomes lowered. In order to use the sterilization apparatus using the electron beam for a long term, it is necessary to periodically change parts and the like of the sterilization apparatus, resulting in an increase in the running cost. In addition, the use of a specific work piece having a strength against corrosion also results in a cost increasing, thus providing a problem.

Then, there has already been proposed an electron beam irradiation apparatus for preventing the generation of nitrogen oxide by supplying a dried gas into an electron beam irradiation chamber (refer to Patent Publication 1: Japanese Patent Application Laid-open Publication No. 9-222500).

The invention disclosed in the above Patent Publication 1 is an electron beam irradiation apparatus which irradiates a work piece to be treated with the electron beam, which is being conveyed within an irradiation chamber by a conveying means such as a conveyer or the like, and in order to reduce the water content in an atmosphere in the irradiation chamber, gas passing through a drying apparatus is supplied into the irradiation chamber.

Patent Publication 1: Japanese Patent Application Laid-open Publication No. 9-222500

DISCLOSURE OF THE INVENTION

Problem to be solved by the Invention

According to the structure of the above-described Patent Publication 1, the dried gas is injected against the work piece which is conveyed within the irradiation chamber and irradiated with the electron beam. The irradiation chamber of the invention of the Patent Publication 1 has a wide space for conveying the work piece to be irradiated, and when the dried gas is injected onto the work piece in such a wide space, the dried gas is liable to be dispersed entirely in the space, thus lowering the drying efficiency.

The present invention was made to solve such problems as mentioned above and an object thereof is to provide a vessel sterilization apparatus capable of effectively maintaining the dried condition in an electron beam irradiation chamber and suppressing the generation of nitric acid from nitrogen oxide.

Means for solving the Problem

The present invention is provided with an electron beam irradiation device, a vessel conveying device, and a sterilization chamber in which the vessel conveying device is disposed, in which an electron beam irradiation surface of the electron beam irradiation device is positioned so as to direct a conveying path of the vessel conveyed by the vessel conveying device, and the vessel is irradiated with the electron beam so as to be sterilized during conveyance within the sterilization chamber, and is characterized in that the irradiation chamber having an vessel inlet and an vessel outlet, which are opened, is formed within the sterilization chamber so as to surround the irradiation surface of the electron beam irradiation device and the vessel to be irradiated, and a gas supply means for supplying aseptic dry-air into the irradiation chamber to thereby maintain a dried condition in the irradiation chamber.

The invention is characterized in that the vessel sterilization apparatus, of the structure provided with the irradiation chamber, is further provided with a discharge chamber communicating with the outlet of the irradiation chamber and disposed so as to cover a conveying path of the vessel after being subjected to the sterilization and a pressure control means for controlling a pressure in the discharge chamber so as to maintain the pressure in the discharge chamber to be higher than that in the irradiation chamber.

The invention is also characterized in that, in the structure provided with the irradiation chamber, the irradiation chamber is formed with an opened portion, at a wall portion thereof except the vessel inlet and outlet portions, to be opened or closed by open/close means.

The invention is also characterized in that, in the structure provided with the irradiation chamber, the vessel conveying device is provided with a vessel conveyer having an endless structure by continuously connecting a plurality of vessel holding means and also provided with a plurality of rotating transfer members around which the endless vessel conveyer is engaged so as to circularly transfer the vessel holding means, a vessel discharge position is set to the circumferential path of the rotating transfer members so that peripheral edge portions of the rotating transfer members setting the vessel discharge position pass through the irradiation chamber.

The invention is also characterized in that, in the structure provided with the irradiation chamber, the sterilization apparatus further includes a beam absorber disposed in opposition to a front side of the irradiation surface of the electron beam irradiation device in the irradiation chamber and configured to receive the irradiating electron beam and cooling means for cooling the beam absorber, so that the beam absorber heated by the electron beam irradiation is cooled to a temperature not less than the temperature in the sterilization chamber.

The vessel sterilization apparatus according to the present invention has a structure in which an irradiation chamber is disposed so as to surround an irradiation surface of the electron beam irradiation device and a vessel to be irradiated with the electron beam, and aseptic dry air is supplied into a narrow space, so that the atmosphere within the irradiation chamber in the electron beam irradiation is performed can be extremely effectively maintained in a dried condition.

EXPLANATION OF REFERENCE NUMERALS 2 vessel
24 vessel conveying device 28 electron beam irradiation device
29b irradiation surface (window foil)
30 irradiation chamber
30a vessel inlet formed to irradiation chamber
30b opened portion of irradiation chamber
32 discharge chamber
80 gas supply means (dry air supply means)

BEST MODE FOR EMBODYING THE INVENTION

The present invention has a structure such that an electron beam irradiation device is disposed in a manner such that an irradiation surface of the electron beam irradiation apparatus faces a vessel conveying path along which the vessel is conveyed by a vessel conveying device, an irradiation chamber is formed so as to surround the irradiation surface and the vessel as an object to be irradiated, the irradiation chamber has an inlet and outlet for the vessel conveyance, and gas supply means for supplying a dried aseptic gas into the irradiation chamber. According to such a structure, the nitrogen oxide generated by the irradiation of the electron beam is prevented from reacting with water and changing to nitric acid.

Embodiment 1

Hereunder, the present invention will be described with reference to an embodiment shown in the drawings.

Figure 2:
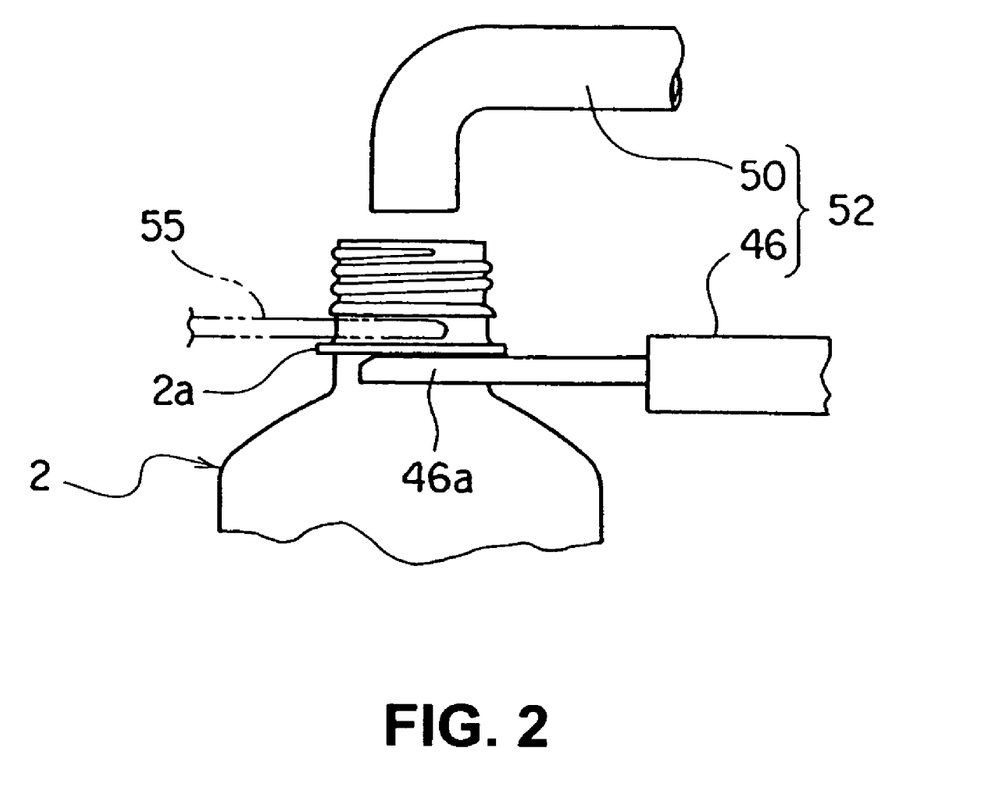
FIG. 2 is a front view showing an essential portion of an air-blower.

In a vessel sterilization apparatus according to this embodiment, a vessel 2 which is filled up with content such as sterilized liquid or like is a PET bottle (see FIG. 2). Such vessels 2 are continuously conveyed by an air conveyer 4, separated from each other at a predetermined interval by an in-feed screw 6, and then, conveyed into an introduction chamber. The introduction chamber is sectioned into two chambers (first introduction chamber 8 and second introduction chamber 10). Rotary wheels (first rotary wheel 12 and second rotary wheel 14) respectively provided with vessel holding means, not shown, are arranged in these chambers 8 and 10, respectively. The vessels 2 conveyed into these introduction chambers 8 and 10 are subsequently transferred to the rotary wheels 12 and 14 in the respective chambers 8 and 10 and then rotated and conveyed. In a wall of the chamber through which the vessel 2 is conveyed from the air conveyer 4 to the first introduction chamber 8, there is formed an opening, not shown, having a size allowing the vessel 2 to pass therethrough, and there is also formed an opening, not shown, through which the vessel 2 is transferred from the first rotary wheel 12 to the second rotary wheel 14, in a partition wall 16 of a vessel transferring portion.

Next to the second introduction chamber 10, there is disposed a sterilization box (sterilization chamber) 18 composed of lead wall sections to shut off the outward leakage of an X-ray (bremsstrahlung) or the electron beam at a time when the vessel 2 is irradiated with the electron beam.

Figure 1:
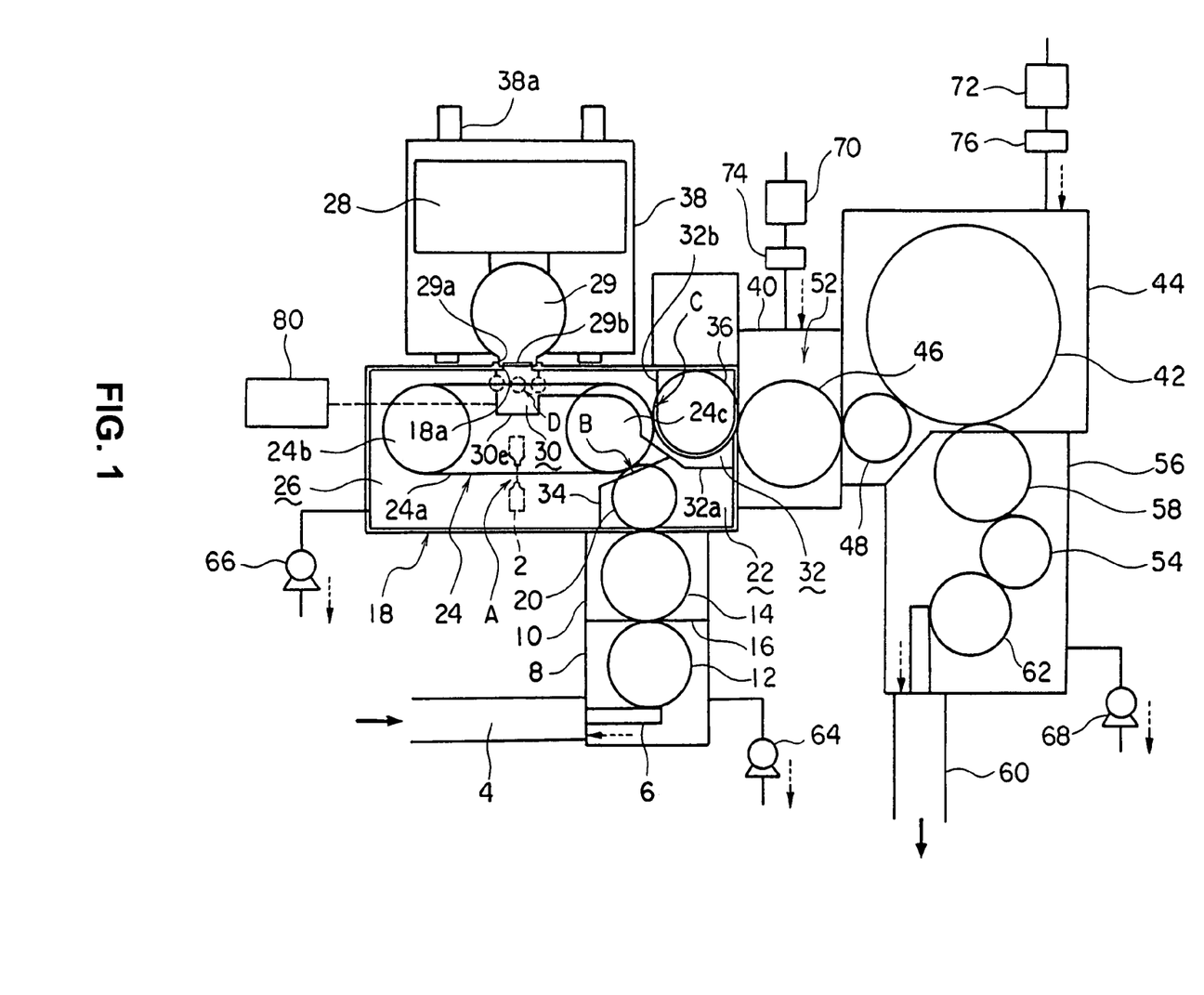
FIG. 1 is a plan view showing the entire structure of a vessel filling system provided with an electron bean sterilization apparatus according to a first embodiment of the present invention (Embodiment 1).

An interior of the sterilization box 18 is divided into some chambers, i.e., an inlet side supply chamber 22 in which a supply wheel 20 is disposed; a main chamber 26 in which a vessel conveying device 24 conveying the vessel 2 received from the supply wheel 20 and turning the vessel upside down; an irradiation chamber 30 which is positioned in front of an electron beam irradiation device 28 and in which the conveying vessel 2 is irradiated with the electron beam; and a discharge chamber 32 which is continuously provided on an outlet side (right side in FIG. 1) of the irradiation chamber 30 and which transfers the vessel 2 sterilized by the electron beam irradiation toward the downstream side while maintaining the aseptic condition.

Furthermore, an opening, not shown, through which the vessel 2 can pass, is formed at a portion of the wall of the sterilization box 18 through which the vessel 2 is transferred from the rotary wheel 14 in the second introduction chamber 10 to the supply wheel 20 in the supply chamber 22. The supply wheel 20 receiving the vessel 2 from the second rotary wheel 14 transfers the vessel 2 to the vessel conveying device 24 in the main chamber 26.

An opening, not shown, allowing the vessel 2 to be transferred therethrough is also formed in a partition wall 34 sectioning the supply chamber 26 and the main chamber 26.

The vessel conveying device 24 disposed in the main chamber 26, though eliminating detailed descriptions of the drawings and the specification, is provided with a vessel holding belt 24a configured as an endless vessel conveyer to which a plurality of vessel grippers as vessel holding means are continuously provided, and two sprockets 24b, 24c, as a transfer rotary member, around which the endless vessel holding belt 24a is engaged for circularly conveying the vessel grippers. The respective vessel grippers are provided with a pair of vertically arranged vessel holding portions to thereby hold and convey two vessels 2, simultaneously, while rotating by 180 degrees around an axis along the conveying direction to thereby take an inverted position.

The vessel conveying device 24 includes a straight path for linearly conveying the vessel grippers between both the sprockets 24b and 24c and a circumferential path extending along the respective sprockets 24b and 24c. An inverting position "A" is set to the straight path from one of the sprockets 24c to the other sprocket 24b, so that the vessel 2 is inverted by one turn during the one time circumferential movement of the vessel 2 to change the vertical position of the vessel 2.

On the other hand, in the circumferential path of the one sprocket 24c, a vessel supplying position "B" is set on the downstream side in the vessel gripper conveying direction, and a vessel discharging position "C" is also set on the upstream side thereof. One vessel 2 is held by one of the vessel holding portion at the supplying position "B" and conveyed by two turns in the circumferential direction, during which the vessel 2 is inverted by two turns in its vertical position, and then, after returning to a position of the vessel supplying time, the vessel 2 is transferred to the transfer wheel 36 of the discharge chamber 32 from the discharging position "C". Further, although the first introduction chamber 8, the second introduction chamber 10, the supplying chamber 22 and the main chamber 26 are maintained at a positive pressure state because the vessel 2 before the sterilization is introduced and conveyed therein, the interiors thereof are not maintained in a completely aseptic condition.

The electron beam irradiation device 28 is disposed adjacent to the sterilization box 18 made of lead. This electron beam irradiation device 28 is provided with an irradiation unit 29 for irradiating the vessel 2 with the electron beam and rests on a mount table 38 to be movable. The structure of this electron beam irradiation device 28 is known, and hence, detailed explanation thereof is not made herein with reference to the drawing and description, but in such a device, generally, a filament is heated in a vacuum condition in the irradiation unit 29 to generate thermoelectrons, the electrons are then accelerated by a high voltage to create thermal high-speed electron beams, which are then taken out, into atmosphere, through the window foil 29b, such as Ti, mounted to the irradiation window 29a, and thereafter, the electron beam irradiation is performed onto a work-piece (i.e., vessel 2 in this embodiment), thus performing a sterilization process.

In this embodiment, the mount table 38 rested with the electron beam irradiation device 28 is disposed to be movable on a rail 38*a* so as to approach or separate from the sterilization box 18. When the vessel charging system is operated, the mount table 38 is moved so as to approach the sterilization box 18, the irradiation window 29*a* of the irradiation unit 29 accords with the opening 18*a* formed in the wall of the sterilization box 18, and then, the sterilization box 18 and the irradiation unit 29 are coupled together.

The irradiation chamber 30 is disposed inside the sterilization box 18 so as to surround the opening 18*a* to which the irradiation unit 29 is fitted. The straight path extending from the sprocket 24*b* to the sprocket 24*c* of the vessel conveying device 24 extends so as to penetrate the irradiation chamber 30, and an irradiating position "D" is set to a penetrating portion of the straight path. Two vessels 2 held by the vessel grippers pass through the irradiation chamber 30 in a vertically perpendicular attitude, and each of the vessels 2 is sterilized by the irradiation of the electron beam from the electron beam irradiation device 28.

In the walls, on the inlet side and outlet side, of the irradiation chamber 30, there are formed openings, not shown, having sizes allowing the two vessels 2 held vertically in attitude by the vessel grippers to pass therethrough. The discharge chamber 32 is formed to be continuous to the wall of the irradiation chamber 30 on the outlet side thereof. One of the sprockets (right side one 24*c* in FIG. 1) of the vessel conveying device 24 is disposed in a state intruding into the discharge chamber 32. The vessel 2 held by the vessel gripper and subjected twice, at vertically upper and lower positions, to the electron beam irradiation is transferred to the transfer wheel 36 disposed in the discharge chamber 32 from the vessel holding portion disposed below the vessel gripper.

The discharge chamber 32 is surrounded, without disturbing the rotation of the sprocket 24*c*, by the partition wall 32*a* sectioning the conveying path, extending from the opening of the outlet side of the irradiation chamber 30 to the transfer wheel 36, of the vessel conveying device 24 and the conveying path of the transfer wheel 36 from the main chamber 26 and the supply chamber 22, the partition wall 32*b* opposing to the partition wall 32*a* and sectioning from the vertical space of the transfer wheel 36 and the bottom surface and ceiling surface of the sterilization box 18. In the respective chambers continuous to this discharge chamber 32, the vessel 2 is sterilized by the irradiation of the electron beam, so that these chambers are maintained in an aseptic condition.

Further, in a preferred modification, it may be possible to section, by locating a partition wall, the conveying path of the vessel conveying device 24 from the outlet side opening of the irradiation chamber 30 to the transfer wheel 36 into an upper conveying space and a lower conveying space without disturbing the conveyance of the vessel 2, and also to section, by locating a partition wall, the conveying path of the transfer wheel 36 from the upper conveying space by communicating with the lower conveying space receiving the vessel 2. In this modified arrangement, the discharge chamber 32 may be formed from a space surrounding the lower conveying space and the conveying path of the transfer wheel 36.

An intermediate chamber 40 is disposed adjacent to the discharge chamber 32 positioned on the most downstream side in the sterilization box 18, and a chamber (filling chamber) 44, in which a filler (filling means) is housed, is provided on the downstream side of this intermediate chamber 40. A rotary wheel (neck wheel) 46 provided with vessel holding means 46*a* (FIG. 2) is disposed inside the intermediate chamber 40, and the neck wheel 46 is operated so as to transfer the vessel 2, received from the transfer wheel 32 in the discharge chamber 32 and then rotated and conveyed, to a supply wheel 48 in the chamber 44 in which the filler 42 is disposed.

Air injection nozzles 50 are arranged, as shown in FIG. 2, above the vessel holding means 46*a*, respectively, at equal intervals in the circumferential direction of the neck wheel 46 disposed in the intermediate chamber 40. The neck wheel 46, the vessel holding means 46*a* and the air injection nozzles 50 constitute an air blower device 52. The air blower device 52 serves to blow aseptic air into the vessel 2 from the air injection nozzle 50 during a time when the vessel 2 is rotated and conveyed in a state in which a lower side of a flanged portion 2*a* formed at the neck portion of the vessel 2 is supported by the vessel holding means 46*a*. As mentioned above, by blowing the aseptic air into the vessel 2 which has been sterilized by the irradiation of the electron beam from the electron beam irradiation device 28, ozone generated by the irradiation of the electron beam is discharged outward from the vessel 2.

Further, grippers 55 (shown with virtual lines in FIG. 2) gripping the upper portion of the flanged portion 2*a* of the vessel 2 are provided, respectively, for the transfer wheel 36 transferring the vessel 2 to the neck wheel 46 and the downstream side supply wheel 48 receiving the vessel 2 from the neck wheel 46.

The vessel 2 after being subjected to the air blowing by the air blower device 52 is transferred to the supply wheel 48 disposed on the inlet side in the chamber 44 and then supplied to the filler 42 disposed in the chamber 44. The filler 42 receiving the vessel 2 from the supply wheel 48 fills the vessel 2 with an inner content such as liquid during the rotating and conveying operations of the vessel 2 in the held state. After the completion of the filling, the vessel 2 is conveyed into a chamber 56 for a capper 54 disposed adjacent to the chamber 44 with the filler 42. An intermediate wheel 58 for receiving the vessel 2 from the filler 42 and transferring the vessel 2 to the capper 54 is disposed on the inlet side of the chamber 56.

Further, on the downstream side of the capper 54, is a discharge wheel 62 for transferring the vessel 2 after being capped to a discharge conveyer 60.

In the vessel filling system of the structure mentioned above, the vessel 2 conveyed by the air conveyer 4 is sterilized in the sterilization box 18 by being irradiated with the electron beam from the electron beam irradiation device 28, then filled up with the inner content by the filler 42, capped by the capper 54, and thereafter, discharged by the discharge conveyer 60 so as to be subjected to the following procedure.

Further, openings through which the vessel can pass are formed respectively in the wall portions at a position at which the vessel 2 is transferred from the transfer wheel disposed in the discharge chamber 32 in the sterilization box 18 to the rotary wheel 46 to the intermediate chamber 40, at a position at which the vessel 2 is transferred from the rotary wheel 46 in the intermediate chamber 40 to the supply wheel 48 in the chamber 44 in which the filler 42 is disposed, and at a position at which the vessel 2 is transferred from the filler 42 to the intermediate wheel 58 disposed in the chamber 56 in which the capper 54 is disposed.

Furthermore, shutters are provided for the respective openings formed in the sterilization box 18 so as to be closed at a time of cleaning the chambers communicating with the inside of the sterilization box 18 to thereby prevent water drops or moisture from entering thereinto.

Air exhaust blowers 64, 66 and 68 are connected respectively to the first introduction chamber 8, the main chamber 26 of the lead sterilization box 18 and the chamber 56 in which the capper 54 is disposed so as to exhaust air in the respective chambers 8, 26 and 56. Further, pressurized air supply means 70 and 72 are connected respectively to the intermediate chamber 40 in which the air blower device 52 and the chamber 44, in which the filler 42 is disposed, through filters 74 and 76, respectively so as to supply aseptic air into the respective chambers 40 and 44. The respective exhaust blowers 64, 66 and 68, the pressurized air supply means 70 and 72, and a control device, not shown, controlling the air exhaust amount and air supply amount constitute a pressure control means, by which the pressures in the respective chambers 8, 10, 22, 26, 32, 40, 44 and 56 are controlled.

In this embodiment, the inside of the intermediate chamber 40 disposed between the sterilization box 18 including the irradiation chamber 30 in which the sterilization of the vessel 2 by the irradiation with the electron beam and the chamber 44 in which the filler 42 is disposed is controlled so as to provide the highest pressure. Moreover, a pressure in the inside of the chamber 44 in which the filler 42 is disposed is controlled to be equal to or slightly lower than the pressure in the intermediate chamber 40.

Further, the inside of the chamber 56, in which the capper 54 is disposed, disposed on the downstream side of the chamber 44 in which the filler 42 is disposed, is controlled so as to provide a pressure lower than the pressure in the chamber 44. On the other hand, a pressure in the inside of the discharge chamber 32 in the sterilization box 18 disposed on the upstream side of the intermediate chamber 40 is controlled so as to provide a pressure lower than the pressure in intermediate chamber 40, and pressures in the irradiation chamber 30 and the main chamber 26 are lower than that in the discharge chamber 32.

Furthermore, pressures in the inside of the supply chamber 22, the second introduction chamber 10 and the first introduction chamber 8, which are disposed on the upstream side of the main chamber 26, provide positive pressures more than that of the outside, but the pressures are controlled so as to become gradually lower toward the upstream side thereof. Furthermore, although the sterilization chamber denotes the sterilization chamber 18, the inside of the intermediate chamber 40 is controlled so as to provide a pressure higher than the pressure in the downstream-side discharge chamber 32 the inside of which is maintained so as to provide the highest pressure in the sterilization box 18. Still furthermore, a blow-out port of the dry-air supply means 80 is connected to the irradiation chamber 30 so as to supply the dried aseptic air.

An operation of the vessel sterilization device of the structures mentioned above will be explained hereunder.

The vessel 2, which is to be sterilized and filled up with inner content, is a PET bottle, and the PET bottle 2 is held by holding the lower side of the flanged portion 2a formed to the neck portion thereof and conveyed by the air conveyer 4 by blowing the air from the rear side of the PET bottle 2. The vessels 2 conveyed by the air conveyer 4 enter into the first introduction chamber 8, in which the vessels 2 are separated at a constant interval and then transferred to the vessel holding means of the first rotary wheel 12. Further, the vessels 2 are rotated and conveyed by the first rotary wheel 12, and then, transferred to the second rotary wheel 14 disposed in the second introduction chamber 10.

Each of the vessels 2 is then transferred to the supply wheel 20 disposed inside the supply chamber 22 of the lead sterilization chamber 18 from the second rotary wheel 14, and rotated, conveyed and then transferred to the gripper of the vessel conveying device 24 in a state held by the vessel holding means of the supply wheel 20. The gripper has upper and lower two vessel gripping portions, and the vessel 2 held by the lower vessel holding portion moves upward and turns upside down by inversely turning the gripper to thereby take an inverted state. The inverted vessel gripper is moved so as to turn around the periphery of the sprocket 24b and enters into the irradiation chamber 30. In the irradiation chamber 30, the vessel 2 is irradiated with the electron beam generated by the electron irradiation device 28 disposed outside the irradiation chamber 30. The vessel 2 conveyed is irradiated with the electron beam and sterilized during the passing forward of the irradiation face (window foil 29b) of the irradiation unit 29.

The vessel 2 subjected to the first irradiation with the electron beam passes throughout the irradiation chamber 30, moves inside the discharge chamber 32, turns around the periphery of the sprocket 24c and then returns to the vessel supply position "B" from the supply wheel 20. The vessel 2 which was received by the lower side vessel holding portion in the preceding operation, mentioned above, from the supply wheel 20 has been turned to an upper position, and hence, the other vessel holding portion disposed on the lower side receives this time the vessel 2 from the supply wheel 20. Thereafter, the gripper is again turned upside down so that the vessel subjected to the irradiation of the electron beam at the upper position and is moved to the lower side, and in this state, the surface which is not irradiated with the electron beam faces the outer side in the rotating direction of the vessel conveying device 24.

When the vessel 2 again enters into the irradiation chamber 30, the vessel 2 subjected to the first (primary) irradiation is subjected to the second (secondary) irradiation with the electron beam from the side opposite to the primary irradiation side, thus the entire inside and outside surface areas of the vessel are sterilized. Simultaneously, the vessel 2 positioned on the upper side and held by the other vessel holding portion is subjected to the first irradiation with the electron beam.

The vessel 2 of which the entire inside and outside surfaces are sterilized by the second irradiation with the electron beam in the irradiation chamber 20 is transferred to the transfer wheel 36 in the discharge chamber 32, then transferred to the neck wheel 46 in the intermediate chamber 40 and discharged thereafter from the lead sterilization box 18. During the rotating and conveying, the aseptic air is injected, from the air injection nozzle 50 disposed upside, inside the vessel 2 held by the vessel holding means 46a of the neck wheel 46 disposed in the intermediate chamber 40, and thereby, the ozone generated by the irradiation with the electron beam and remaining inside the vessel 2 is exhausted.

The vessel 2 held by the neck wheel 46 of the intermediate chamber 40 is thereafter transferred to the supply wheel 48 disposed inside the chamber 44 in which the filler 42 is disposed. Thereafter, the vessel 2 is supplied to the filler 42 from the supply wheel 48. The vessel 2 filled up with the inner content by the filler 42 during the rotation and conveyance is taken out from the filler 42 by the intermediate wheel 58 and then conveyed into the chamber 56 in which the capper 54 is disposed. The vessel 2 conveyed inside the chamber 56 is transferred to the capper 54 from the intermediate wheel 58 and subjected to the capping operation, and thereafter, the vessel is discharged on the discharge conveyer 60 through the discharge wheel 62 to be subjected to the next process.

The dry-air supply means 80 is connected to the irradiation chamber 30 so as to supply the dried aseptic air. As mentioned hereinbefore, when the electron beam irradiation device irradiates the irradiation chamber with the electron beam, nitrogen oxide is generated, and if water content exists in the irradiated environment, the nitrogen oxide is dissolved into water to thereby produce nitric acid, which may corrode the metal parts of the vessel conveying device 24.

Then, the irradiation chamber 30 is provided in the sterilization box 18, and the dry-air is introduced into this irradiation chamber 30 to maintain the dried condition therein, thereby preventing the nitric acid from generating and preventing the metal parts from being corroded.

Particularly, in this embodiment, only the peripheral portion of the vessel 2, which is an object to be irradiated and passes the irradiation surface of the electron beam irradiation device 28, i.e., the front surface side of the irradiation window 29a to which the window foil 29b is attached, is accommodated in the irradiation chamber 30 so as to be surrounded.

The irradiation chamber 30 is defined by a wall portion continuing from the floor surface of the sterilization box 18 to the ceiling thereof, except the openings forming the inlet 30a (FIG. 3) for the vessel 2 conveyed by the vessel conveying device 24 and an outlet, not shown. These openings formed as the inlet and outlet have necessarily the smallest areas for the passing of the vessel 2 of a size almost closed by the vessel 2 when the vessel 2 passes through the openings at the time of the sterilization. Thus, since the dried-air can be supplied into the narrow space having a high closing performance, the space into which the electron beam irradiation is performed can be effectively dried. Further, as a drying gas to be supplied in the irradiation chamber 30, a gas having high drying performance and a dew point of −30 to −40° C. In this operation, the atmosphere is dried and the aseptic space is created, so that running cost of the apparatus can be low.

Furthermore, in the sterilization device using the electron beam, it is conventionally known to sterilize a sterilization apparatus or sterilizer itself by utilizing X-rays or ozone generated by the electron beam irradiation (Japanese Patent Publication No. 52-17469, Japanese Patent Application Laid-open Publication No. 8-89562, etc.).

Figure 3:
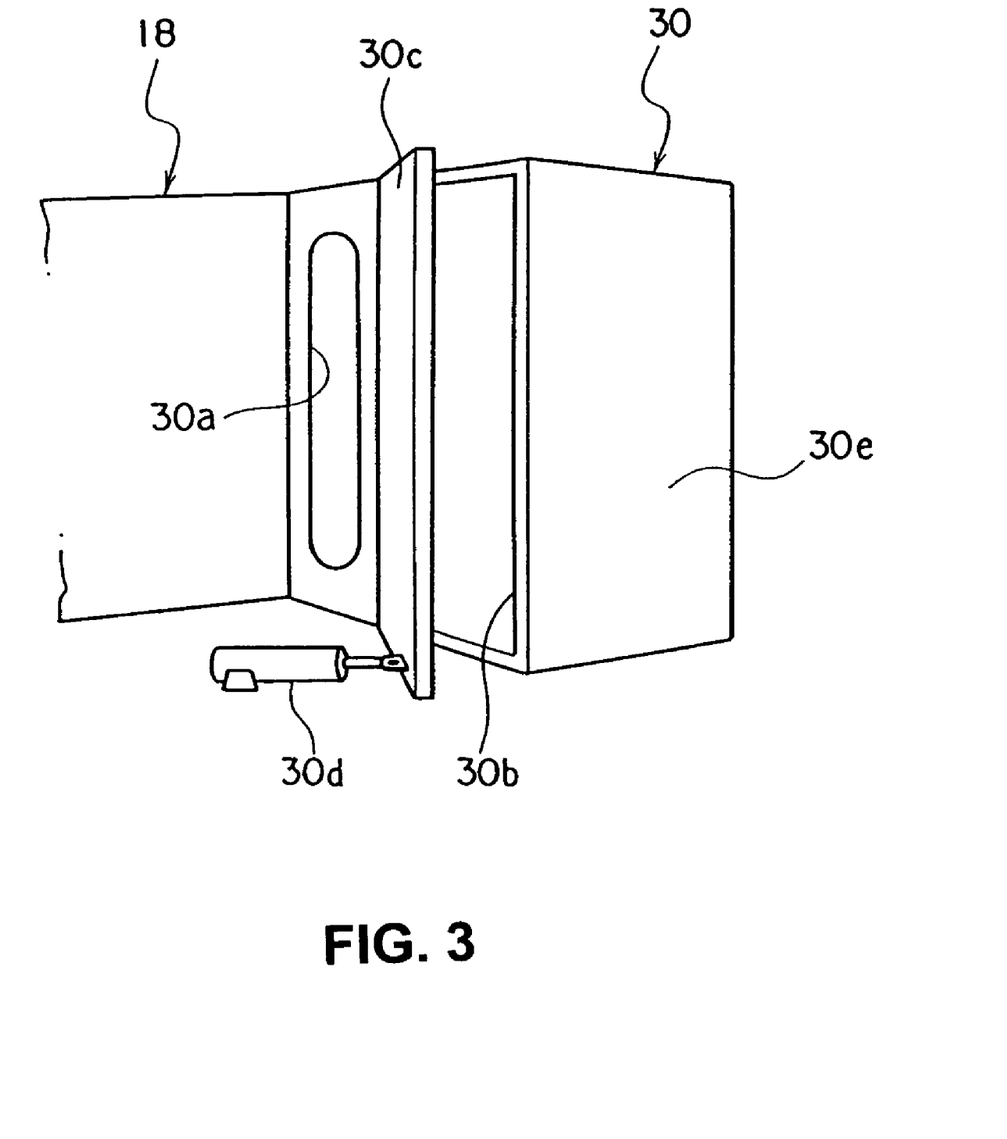
FIG. 3 is a perspective view showing a structure of an irradiation chamber.

However, with the structure of this embodiment, since a portion which is subjected to the sterilization by the electron beam irradiation onto the vessel 2 is surrounded by a wall as the irradiation chamber 30, the X-ray or ozone generated by the electron beam or electron beam irradiation is not sufficiently spread within the sterilization box 18. Then, as shown in FIG. 3, both the side wall portions of the irradiation chamber 30, i.e., wall portions except the wall portions to which the inlet 30a through which the vessel 2 is conveyed into the irradiation chamber 30 by the vessel conveying device 24 and to which the outlet through which the vessel 2 is conveyed outward, are formed as opened portions 30b (opened portion on the outlet side is not shown) so that the opened portions are opened or closed by open/close means (doors) 30c. These side doors 30c are opened or closed by an air cylinder. By opening these doors 30c, the X-rays or ozone generated by the electron beam irradiation having the sterilizing function may be spread entirely within the sterilization box 18. According to the structure of this embodiment, the interior of the irradiation chamber 30 and the vessel conveying device 24 passing through the irradiation chamber 30 are sterilized by the direct electron beam irradiation during the time of sterilization of the vessel 2.

However, since other portions in the sterilization box 18 are not irradiated with the electron beam, the sterilization will be performed by sufficiently spreading the electron beam, the X-ray or ozone generated by the electron beam irradiation device 28 periodically after the completion of the sterilization working within the sterilization box 18 by flowing outward through the opened portion 30b, in a state of the doors 30c of the opened portions 30b of both the side wall portions being opened, by operating the open/close air cylinder 30d as occasion demands. Further, in this operation, in order to prevent the nitric acid from being generated, before the electron beam irradiation, the doors 30c are opened in the opened state of the opened portions 30b, the dry-air is supplied from the dry-air supply means 80, and the dry-air is then blown out through the irradiation chamber 30 to create the dried condition in the sterilization box 18. During the dry-air supply, the electron beam irradiation is performed.

The wall portion (inner surface side of a lower side wall portion 30e in FIG. 1) of the irradiation chamber 30 opposing the front surface of the irradiation window 29a of the electron beam irradiation device 28 is provided as a metallic beam absorber receiving the electron beam irradiation, and by this beam absorber, the irradiating electron beam or generated X-ray is shielded to prevent unnecessary irradiation to a back side.

Further, the beam absorber is heated to a very high temperature by means of continuous direct irradiation of the electron beam during the sterilization of the vessel 2, so that it is necessary to cool the beam absorber. Because of this reason, a conduit is entirely embedded inside the wall portion 30e of the irradiation chamber 30 functioning as the beam absorber for circulating cooling water as cooling means to thereby entirely cool the wall portion 30e.

Then, in this embodiment, the opened portions 30b are formed in both the side wall portions opposed to the irradiation windows 29e and the wall portion 30e so as not to form the opened portions 30b to the front wall portion 30e of the irradiation windows 29e of the electron beam irradiation device 28 to which the opened portions are not formed because of the embedment of the conduit. Furthermore, the bremsstrahlung can be effectively generated by the collision of the irradiated electron beam against the beam absorber made of metal.

Still furthermore, the beam absorber may generate dew on inner and outer surfaces of the wall portion 30e depending on a cooling temperature, which may result in the generation of nitric acid and, therefore, the beam absorber is cooled at a temperature not less than the temperature inside of the sterilization box 18. Further, at the time of the electron beam irradiation, the temperature inside the sterilization box 18 increases about 40° C., but the beam absorber is not so cooled to about 50 to 60° C. by using the cooling water having about a room temperature (15 to 20° C.) near ambient temperature and, moreover, any dew is not caused, even in a state of no electron beam irradiation and no increase in the temperature.

Embodiment 2

Figure 4:
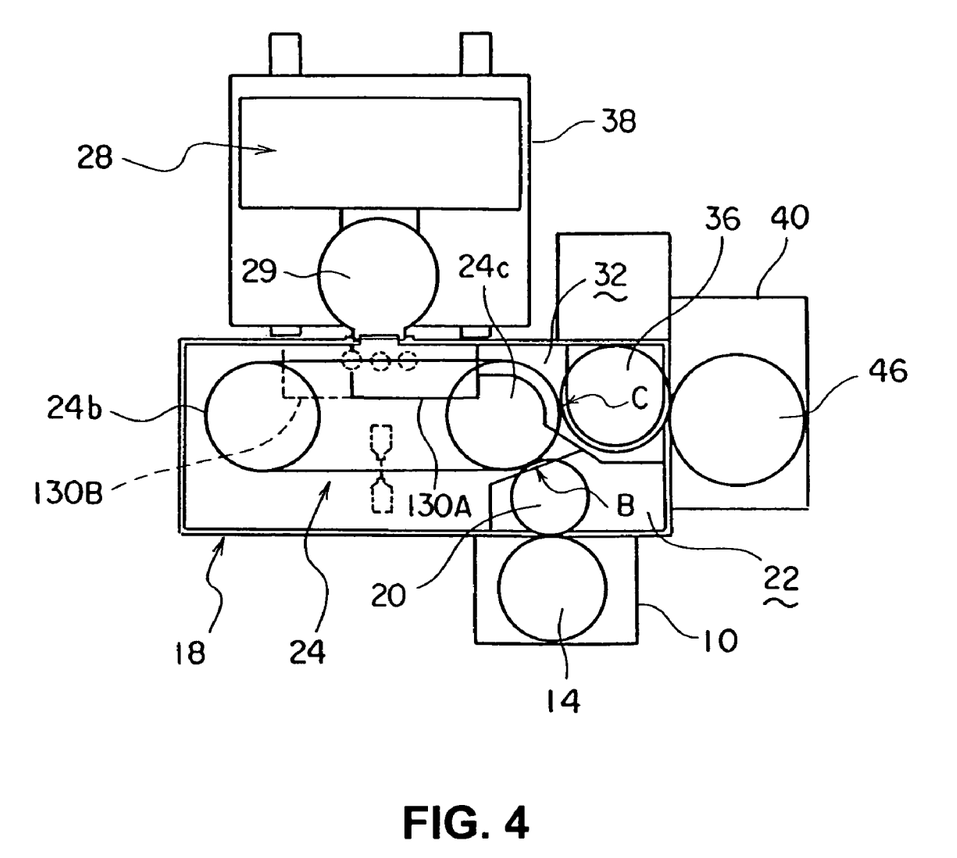
FIG. 4 is a plan view showing an essential portion of a vessel sterilization apparatus according to a second embodiment of the present invention (Embodiment 2).

FIG. 4 represents a modified embodiment of the embodiment mentioned above, in which the structure of an irradiation box 130 of the sterilization box 18 of this embodiment 2 differs from that of the first embodiment. Further, since the other structures are substantially the same as those of the first embodiment, the same reference numerals are added to corresponding members or the like and a duplicated explanation will be omitted hereunder, and only the different portions are explained.

That is, the vessel grippers directly contacting the vessels 2 in the structure of the vessel conveying device 24 of the afore-mentioned embodiment are provided for the vessel holding belt 24a formed in an endless fashion, and the vessels 2 are irradiated with the electron beam and sterilized during the circularly conveyance in and passing through the irradiation chamber 130 to thereby maintain cleanliness during the sterilization working to the vessels 2. However, the sterilization working may not be achieved to the other structural portions. Particularly, the sprocket 24c to which the vessel supply position "B" and the discharge portion "C" is disposed adjacent to the transfer wheel 36 and the peripheral portion of the sprocket 24c may enter into the discharge chamber 32 the interior of which is maintained at the aseptic condition. Therefore, although a high cleanliness is required for this portion, there is a high possibility of contaminating this portion because of adjacently contacting the supply wheel 20 supplying the vessels 2 from an exterior side. Then, in this embodiment, the size of the irradiation chamber 130 is enlarged toward the vessel conveying direction. For example, as shown with solid line 130A in FIG. 4, a wall portion of the irradiation chamber 130A to which the vessel outlet is formed is extended on the side of the discharge chamber 32, and in this state, the discharge chamber 32 is retired by a distance corresponding to the extended portion of the irradiation chamber 130A.

As mentioned above, by extending the irradiation chamber 130A, the peripheral edge portion of the sprocket 24c of the vessel conveying device 24 can be housed in the irradiation chamber 130A, and accordingly, the peripheral edge portion of the sprocket 24c gets closer to the supply wheel 20 and the atmosphere in the supply chamber 22 at the supply position "B" and then the peripheral edge portion of the sprocket 24c can pass through the irradiation chamber 130A in accordance with the rotation of the sprocket 24c. The sterilization function is achieved and the cleanliness during the passing therethrough is also achieved by the influence of the electron beam or X-ray irradiation, and hence, the contamination can be prevented from progressing. Thereafter, the vessel 2 passes through the irradiation chamber 130A, enters into the discharge chamber 32 and reaches the discharge position "C", so that even if there is a fear that any germ or contaminating substance may adhere to the peripheral edge portion of the sprocket 24c at a portion near the supply position "B", the germ or contaminating substance can be prevented from entering into the discharge chamber 32, and hence, the discharge chamber 32 and the other chambers disposed downstream side thereof are free from contamination.

Further, as shown with the broken line in FIG. 4, an irradiation chamber 130B may be extended by moving the wall portion to which the inlet is formed toward the upstream side. In such an embodiment, the peripheral edge portion of the other sprocket 24b may enter into the irradiation chamber 130B to thereby achieve the sterilization function.

Furthermore, it may be also possible to extend both the upstream and downstream sides of the irradiation chamber by moving both the wall portions on the inlet and outlet sides of the irradiation chamber (in a combined state of the irradiation chambers 130A and 130B). In this arrangement, the sterilization function may be achieved to the peripheral edge portions of both the sprockets 24b and 24c.

The invention claimed is:

1. A vessel sterilization apparatus comprising an electron beam irradiation device, a vessel conveying device, a sterilization chamber, an irradiation chamber, a discharge chamber, a gas supply means for supplying aseptic dry air into the irradiation chamber and maintaining it in a dried condition and a pressure control means for controlling and maintaining the pressure in the discharge chamber to be higher than the pressure in the irradiation chamber, the vessel conveying device being disposed in the sterilization chamber and the sterilization chamber preventing the exiting of X-rays and electron beams therefrom, the electron beam irradiation device having an electron beam irradiation surface positioned for irradiating a conveying path of a vessel conveyed by the vessel conveying device so that the vessel is irradiated with an electron beam and sterilized during its conveyance within the sterilization chamber, the irradiation chamber having a vessel inlet and a vessel outlet and being formed within the sterilization chamber to surround the irradiation surface of the electron beam irradiation device and the vessel to be irradiated and the discharge chamber communicates with the vessel outlet of the irradiation chamber and covers a conveying path of the vessel after the vessel has been sterilized.

2. The vessel sterilization apparatus according to claim 1, wherein the irradiation chamber is formed with an opened portion, at a wall portion thereof, other than the vessel inlet and outlet portions, which is opened and closed by an open/close means.

3. The vessel sterilization apparatus according to claim 1, wherein the vessel conveying device is provided with a vessel conveyer having an endless structure by continuously connecting a plurality of vessel holding means and also provided with a plurality of rotating transfer members around which the endless vessel conveyer is engaged so as to circularly transfer the vessel holding means, a vessel discharge position is set at a circumferential path of the rotating transfer members so that peripheral edge portions of the rotating transfer members setting the vessel discharge position pass through the irradiation chamber.

4. The vessel sterilization apparatus according to claim 1, further comprising a beam absorber disposed opposite to a front side of the irradiation surface of the electron beam irradiation device in the irradiation chamber and configured to receive the irradiating electron beam and cooling means for cooling the beam absorber, so that the beam absorber, heated by the electron beam irradiation, is cooled to a temperature not less than the temperature in the sterilization chamber.

* * * * *